United States Patent [19]
Pappas

[11] Patent Number: 5,683,468
[45] Date of Patent: Nov. 4, 1997

[54] MOBILE BEARING TOTAL JOINT REPLACEMENT

[76] Inventor: Michael J. Pappas, 61 Gould Pl., Caldwell, N.J. 07006

[21] Appl. No.: 404,179

[22] Filed: Mar. 13, 1995

[51] Int. Cl.$^6$ .................................................. A61F 2/38
[52] U.S. Cl. ............................................................ 623/20
[58] Field of Search ................................ 623/16, 18, 20

[56] References Cited

U.S. PATENT DOCUMENTS

| | | |
|---|---|---|
| 4,085,466 | 4/1978 | Goodfellow et al. . |
| 4,219,893 | 9/1980 | Noiles . |
| 4,309,778 | 1/1982 | Buechel et al. . |
| 4,340,978 | 7/1982 | Buechel et al. . |
| 4,728,332 | 3/1988 | Albrertsson .................... 623/20 |
| 4,950,298 | 8/1990 | Gustilo et al. .................. 623/20 |
| 5,071,438 | 12/1991 | Jones et al. ..................... 623/20 |
| 5,282,868 | 2/1994 | Bahler ............................ 623/20 |
| 5,330,533 | 7/1994 | Walker ........................... 623/20 |

FOREIGN PATENT DOCUMENTS

| | | |
|---|---|---|
| 0 346 183 | 12/1989 | European Pat. Off. . |
| 0529408 | 3/1993 | European Pat. Off. ......... 623/20 |
| 0634155 | 1/1995 | European Pat. Off. ......... 623/20 |
| 0 636 353 A1 | 2/1995 | European Pat. Off. . |
| 2672798 | 8/1992 | France ............................ 623/20 |
| 2 061 730 | 5/1981 | United Kingdom . |
| 2184025 | 6/1987 | United Kingdom ............ 623/20 |
| 9208424 | 5/1992 | WIPO ............................. 623/20 |

*Primary Examiner*—Mary Beth Jones
*Attorney, Agent, or Firm*—Anthony J. Casella; Gerald E. Hespos

[57] ABSTRACT

A prosthetic component is provided for a condylar joint. The prosthetic component includes a platform having a bearing surface and a pair of side walls. The side walls include a pair of concave surfaces which face one another and define arcs of the same right circular cylinder. The prosthetic component also includes a plastic bearing having a bearing surface slidably engaged with the bearing surface of the platform. The bearing also includes thrust surfaces defining arcs of two right circular cylinders having radii less than the radius of the side wall surfaces of the platform. The thrust surfaces are spaced from one another to permit only limited sliding movement of the bearing in medial to lateral directions, but greater sliding movement in anterior to posterior directions.

43 Claims, 7 Drawing Sheets

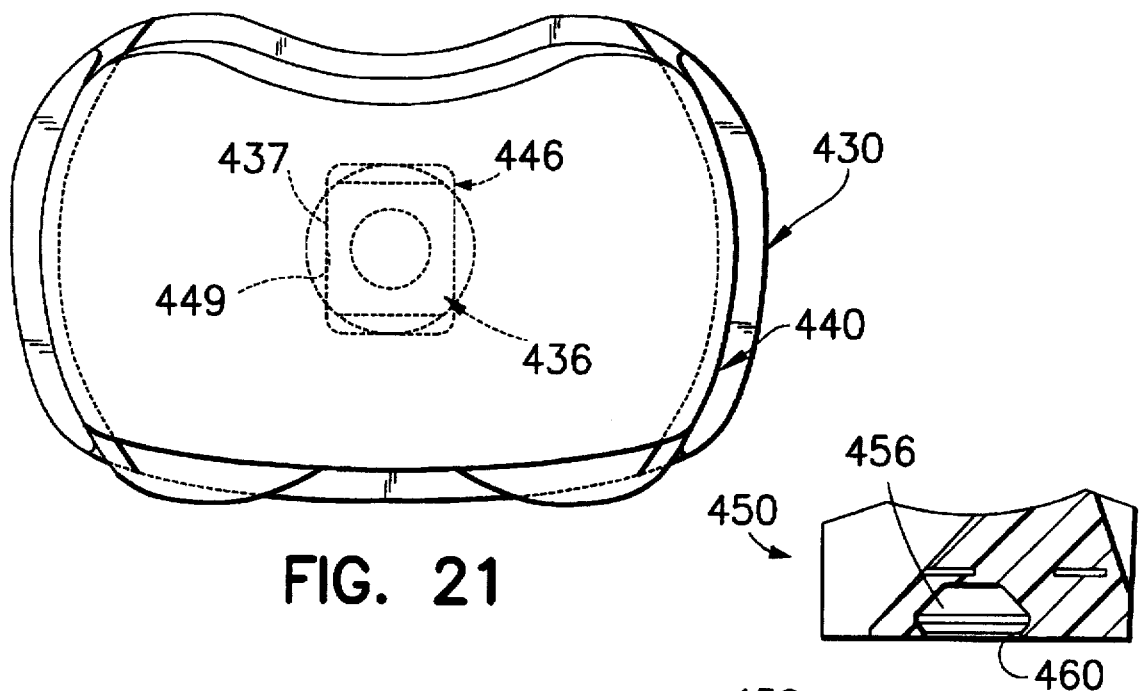
FIG. 21
FIG. 22
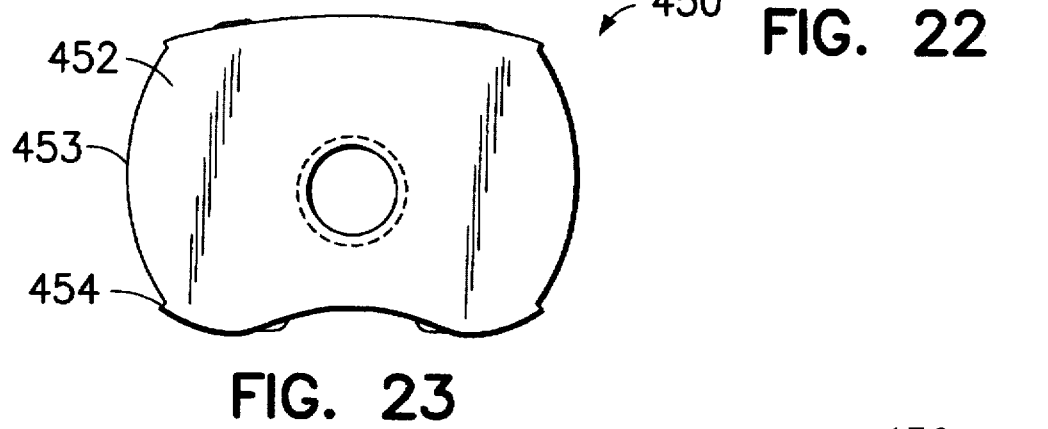
FIG. 23
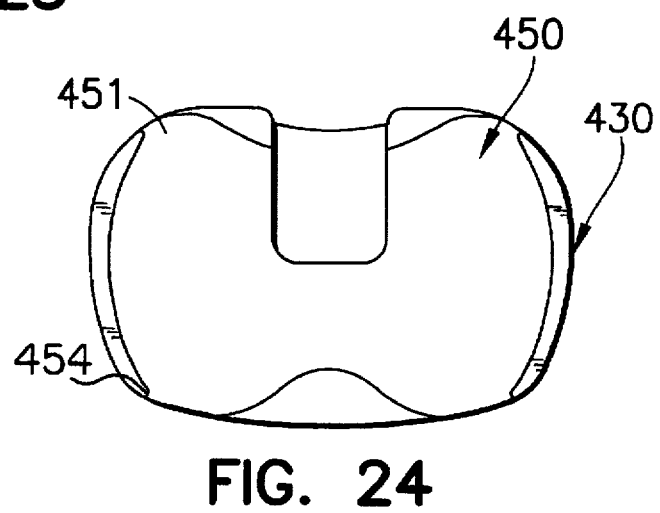
FIG. 24

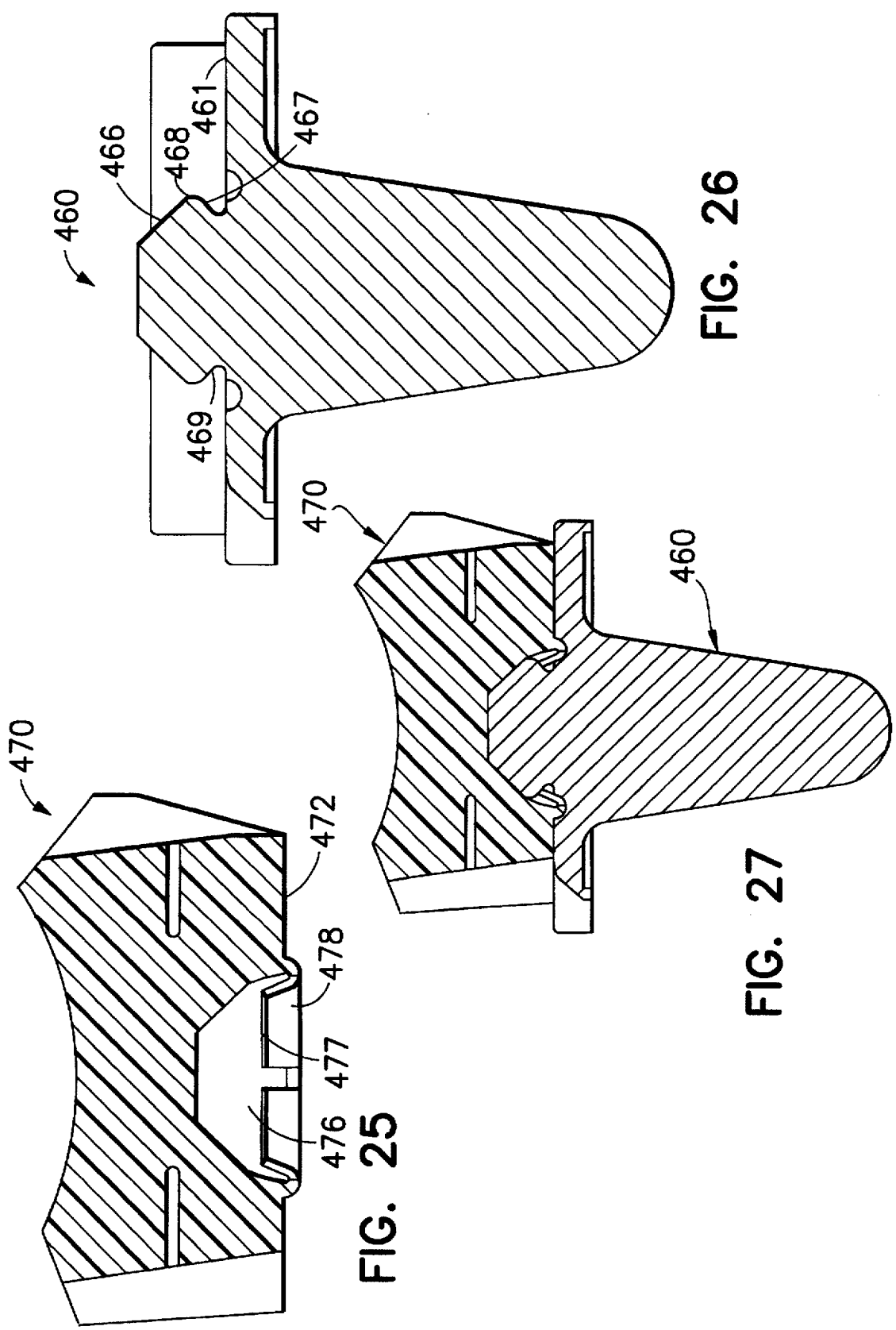

MOBILE BEARING TOTAL JOINT REPLACEMENT

BACKGROUND OF THE INVENTION

1. Field of the Invention

The invention generally relates to mobile bearing total joint replacements, particularly those of the knee.

2. Description of the Prior Art

Prior art mobile bearing total joint replacement prostheses are described in Noiles U.S. Pat. No. 4,219,893, Goodfellow and O'Connor U.S. Pat. No. 4,085,466 and Buechel and Pappas U.S. Pat. Nos. 4,309,778 and 4,340,978. Noiles, in particular describes a mobile bearing knee in which a bearing is retained by side walls of a tibial platform. The inner face of the side walls of the Noiles tibial platform are circular cylinders, as is the complementary side wall of the bearing. Noiles provides a small, uniform clearance that allows some small amount of anterior-posterior (A-P) motion in addition to axial rotation of the bearing relative to the tibial components. This clearance produces medial lateral (M-L) play in the knee roughly equal to the A-P motion, and thus is undesirable. An increase in A-P motion produced by an increase in clearance is undesirable since such an increase produces additional undesirable M-L play. Further the bearing shown by Noiles is retained only by these side walls and the action of the femoral component in concert with the ligaments of the knee. Such restraint may be insufficient to prevent dislocation of the bearing for designs with a larger amount of engagement between the femoral and tibial bearing condyles than that shown by Noiles, or where the ligaments are lax.

The objective of this invention is to increase the amount of A-P motion without increasing the M-L play in the knee and to provide additional means for preventing dislocation of the bearing in those situations where such additional restraint is desirable.

SUMMARY OF THE INVENTION

A prosthetic component is provided for a condylar joint, such as a knee. The prosthetic component includes a metallic platform having an inferiorly disposed bone attachment portion and a superiorly disposed bearing surface. Spaced apart medial and lateral side walls project from the bearing surface. The medial and lateral side walls each include an anterior end, a posterior end and a concave surface extending therebetween. The concave surfaces face one another, and preferably define arcs of a single right circular cylinder having a radius $R_r$.

The prosthetic component of the subject invention further includes a plastic bearing having an inferior bearing surface slidably engaged on the superior bearing surface of the platform. The bearing includes medial and lateral thrust surfaces extending from the inferior bearing surface and defining arcs of two separate right circular cylinders having radii $R_b$ which are less than the radius $R_r$ on the medial and lateral side walls of the platform. The medial and lateral thrust surfaces are spaced from one another distances that permit a minor medial to lateral (M-L) clearance between the thrust surfaces and the respective side walls of the platform. The radii $R_b$ and $R_r$ are selected relative to the M-L clearance to permit greater sliding movement of the bearing in an anterior-to-posterior direction than in a medial-to-lateral direction.

The inferior surface of the bearing may further be characterized by a cavity extending therein. The superior bearing surface of the platform may include a button slidably engaged in the cavity. The relative dimensions of the cavity and the button may be selected to permit the full range of M-L and A-P movement that are controlled by the side walls of the platform. The button and the cavity may include interlocking structure for maintaining the inferior bearing surface of the bearing and the superior bearing surface of the platform in generally abutting sliding engagement with one another.

The provision of thrust surfaces defining arc segments of two right circular cylinders enables the prosthetic component to provide a desirably large range of anterior to posterior movement and a desirably small range of medial to lateral movement between the bearing and the platform.

The invention also is directed to a system of prosthetic components employing a single platform and a plurality of bearings one of which may be selected intra-operatively or during a surgical revision to permit an appropriate range of movement between the bearing and the platform for the particular patient. For example, an alternate bearing to the one described above may permit only minor sliding movement in all directions and rotational movement. In other embodiments the bearing may be constructed to lockingly engage the platform to prevent substantially all movement between the bearing and the platform.

BRIEF DESCRIPTION OF THE DRAWINGS

FIG. 21 is a superior view similar to FIG. 20, but showing the bearing and tibial platform in their fully assembled condition.

FIG. 22 is a saggital cross-sectional view of a third embodiment of a bearing that can be fixedly secured to the tibial component.

FIG. 23 is an inferior view of the bearing shown in FIG. 22.

FIG. 24 shows the bearing of FIG. 22 and 23 fixedly mounted to the tibial component.

FIG. 25 is a saggital cross-sectional view of another alternate bearing.

FIG. 26 is a saggital cross-sectional view of the tibial platform for use with the bearing of FIG. 25.

FIG. 27 is a saggital cross-sectional view of the bearing on FIG. 25 assembled to the tibial platform of FIG. 26.

DETAILED DESCRIPTION OF THE PREFERRED EMBODIMENTS

Figure 1:
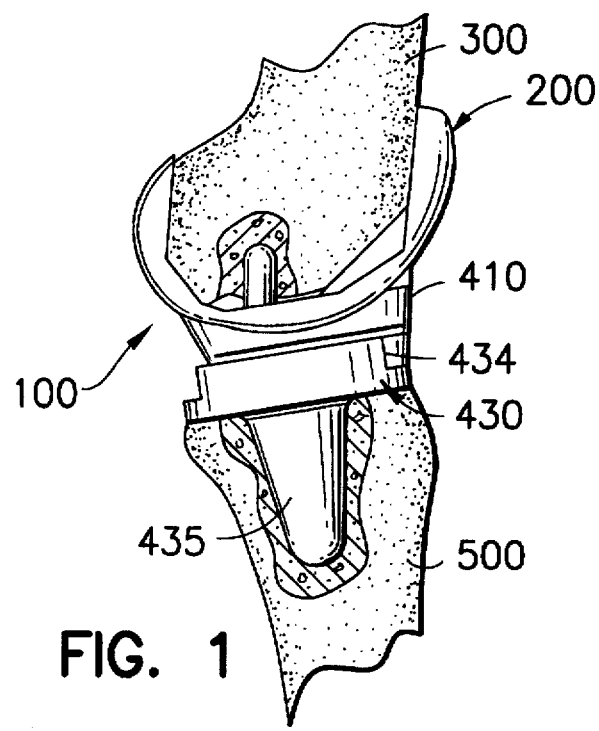
FIG. 1 is a lateral view of a mobile bearing knee replacement in accordance with the subject invention.
Figure 2:
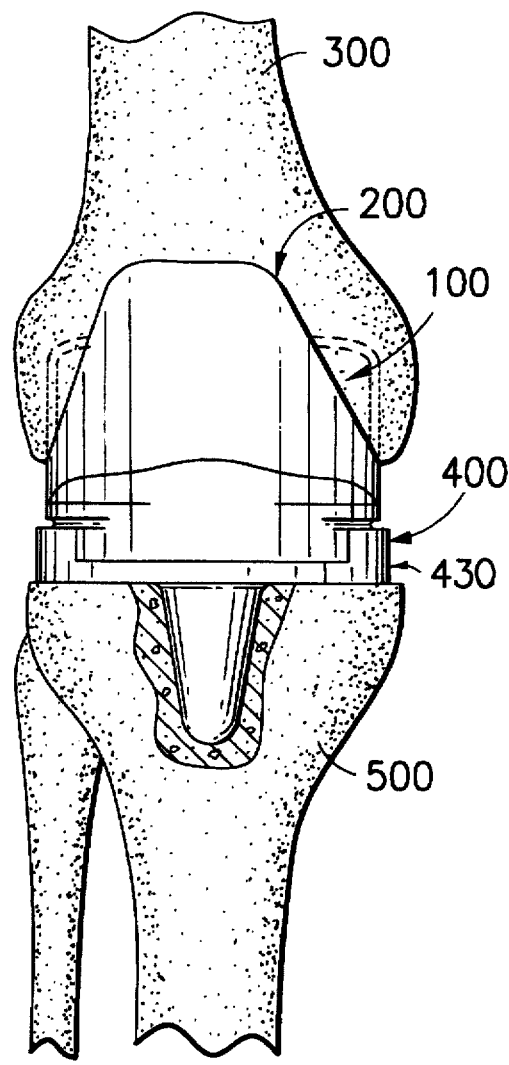
FIG. 2 is an anterior view of the knee replacement shown in FIG. 1.

FIGS. 1 and 2 show lateral and anterior views respectively of the knee replacement 100. The knee replacement 100 consists of a femoral component 200 which is fixtured to the distal femur 300. Metallic femoral component 200 is essentially the same as that described in U.S. Pat. Nos. 4,309,778 and 4,340,978. A tibial component 400 consists a plastic bearing 410 and metallic tibial platform 430 which is fixtured to the proximal tibia 500.

Figure 3:
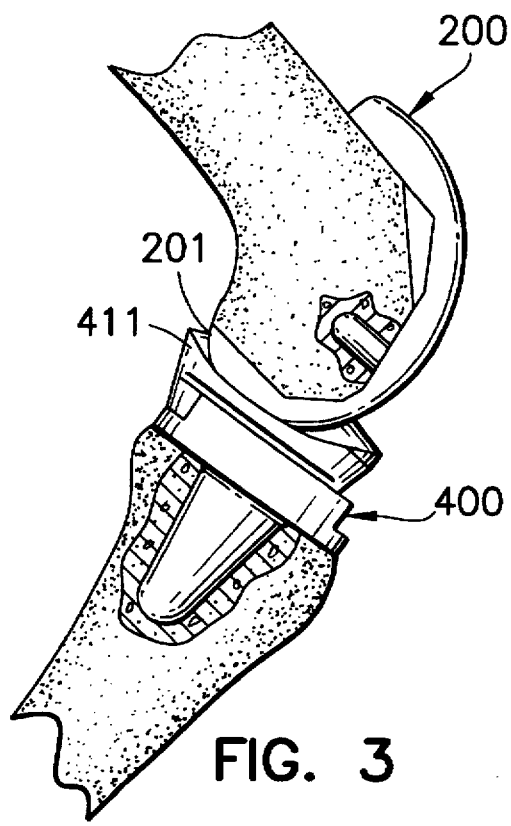
FIG. 3 is a lateral view similar to FIG. 1, but showing the knee replacement at about 90° of flexion.

FIGS. 1 and 3 show a lateral view of the knee replacement in full extension and about 90° of flexion respectively. At full extension the bearing will usually be in an anterior position as shown in FIG. 1. As the knee is flexed, the action of the ligaments in concert with the shape of the femoral articulating surface 201 and the tibial articulating surface 411 generate posterior displacement of the bearing 410 relative to the tibial platform 430 so that the bearing 410 occupies a posterior position as shown in FIG. 3.

Where a mobile bearing, as shown in FIGS. 1 and 3 which moves relative to the tibial platform 430, is employed, the shape of the femoral articulating surface 201 preferably is complimentary, at least for some of the range of flexion of the joint, to the tibial articulating surface 411. A mobile bearing is needed, where these articulating surfaces are congruent, in order to provide motion of the knee approximating normal. A mobile bearing is also useful where there is moderate incongruity of these surfaces. Adequate motion can be obtained, however, with designs where the bearing does not move relative to the tibial platform 430 (fixed bearing). Such fixed bearing designs generally have substantially higher contact stress and wear than mobile bearing designs.

Figure 4:
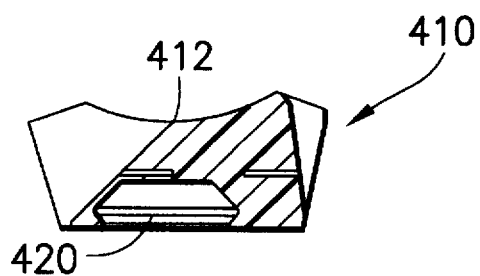
FIG. 4 is a saggital sectional view of a plastic bearing of the tibial component of the knee replacement.
Figure 5:
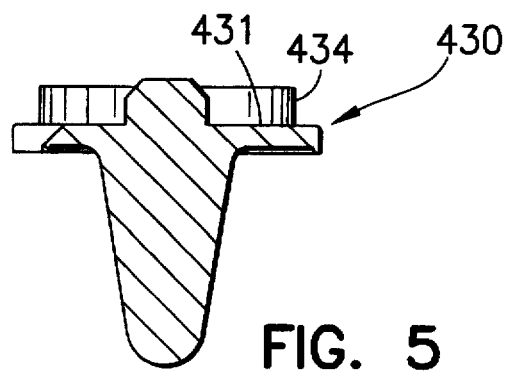
FIG. 5 is a saggital sectional view of the metallic tibial platform of the tibial component of the knee replacement.
Figure 6:
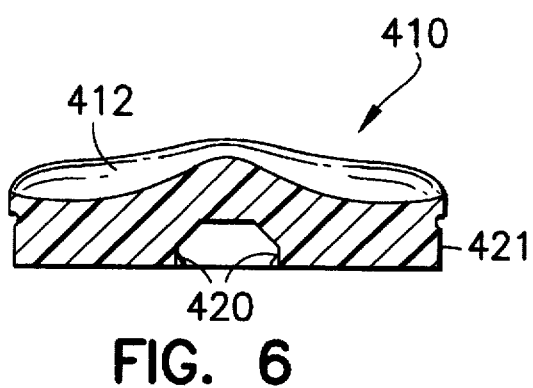
FIG. 6 is a coronal sectional view of the plastic bearing.
Figure 7:
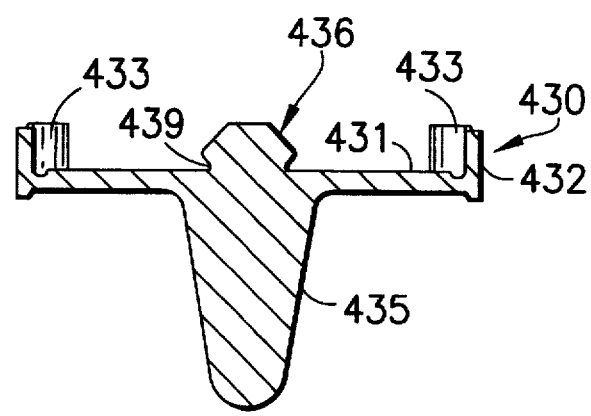
FIG. 7 is a coronal sectional view of the tibial platform.
Figure 8:
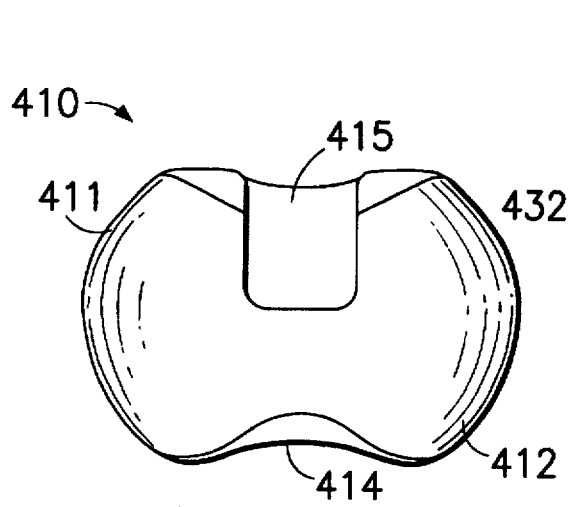
FIG. 8 is a superior view of the plastic bearing.
Figure 9:
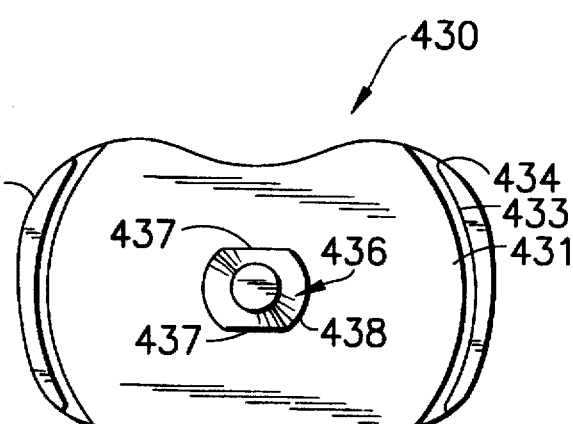
FIG. 9 is a superior view of the tibial platform.
Figure 10:
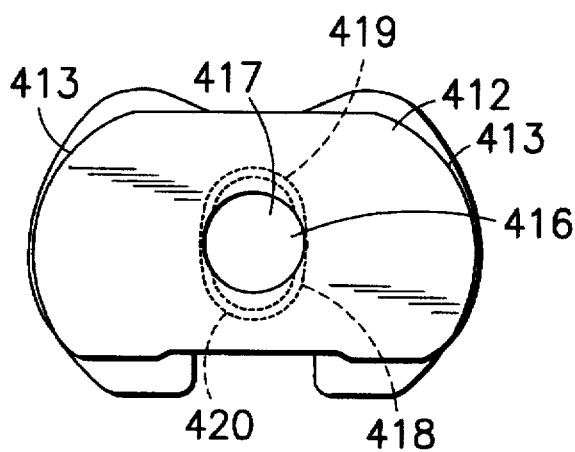
FIG. 10 is an inferior view of the plastic bearing.

FIGS. 4 and 5 show saggital sectional views, FIGS. 6 and 7 coronal sectional views and FIGS. 8 and 9 superior views of the tibial platform 430 and an A-P Glide embodiment of a bearing 410 respectively. FIG. 10 shows an inferior view of the bearing.

The tibial platform 430 consists of a load bearing plate 431, side walls 432 with faces 433 and side wall ends 434 and a fixturing stem 435. The two faces 433 together form segments of the same right circular cylinder of radius $R_r$. Thus any bearing fitting entirely within this cylinder is free to rotate on the load bearing plate 431. This plate may also have a button 436 with two flats 437, button side walls 438 with a recess groove 439. The side walls 433 preferably are disposed at the extreme medial and lateral aspects of the tibial platform in order to provide the largest possible wall radius, thereby minimizing contact stress and maximizing A-P motion.

Figure 11:
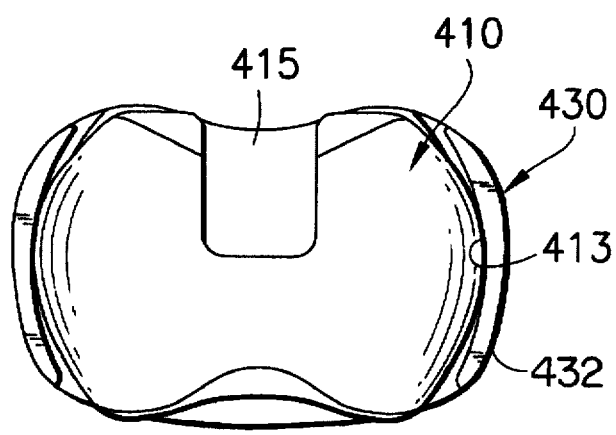
FIG. 11 is a superior view of the assembled tibial component.
Figure 12:
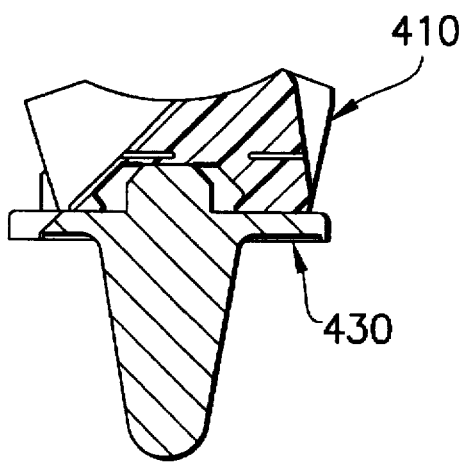
FIG. 12 is a saggital sectional view of the assembled tibial component.
Figure 13:
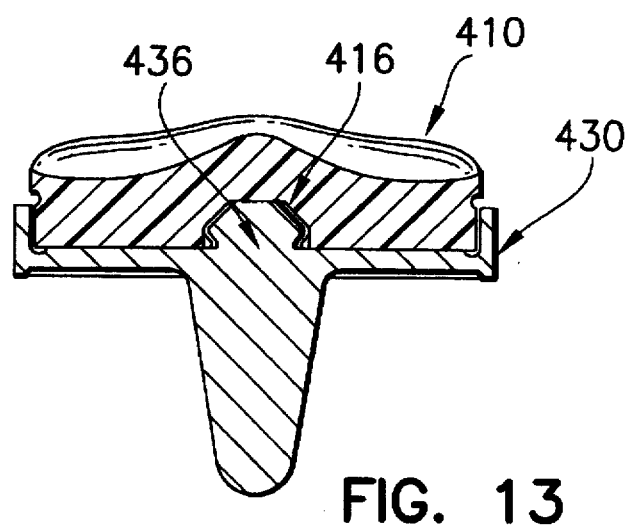
FIG. 13 is a coronal sectional view of the assembled tibial component.

The bearing 410 consists of an inferior bearing surface 412, a tibial articulating surface 411, two thrust surfaces 413 which are segments of two right circular cylinders of radius $R_b$, an anterior recess 414 to clear the patella tendon and a posterior recess 415 to clear to posterior cruciate ligament. The bearing 410 may also have a cavity 416 with a central hole 417, oval side walls 418 and cylindrical ends 419 with ridges 420. FIGS. 11, 12 and 13 show superior and saggital and coronal sections of the assembled bearing and tibial platform respectively.

Figure 14:
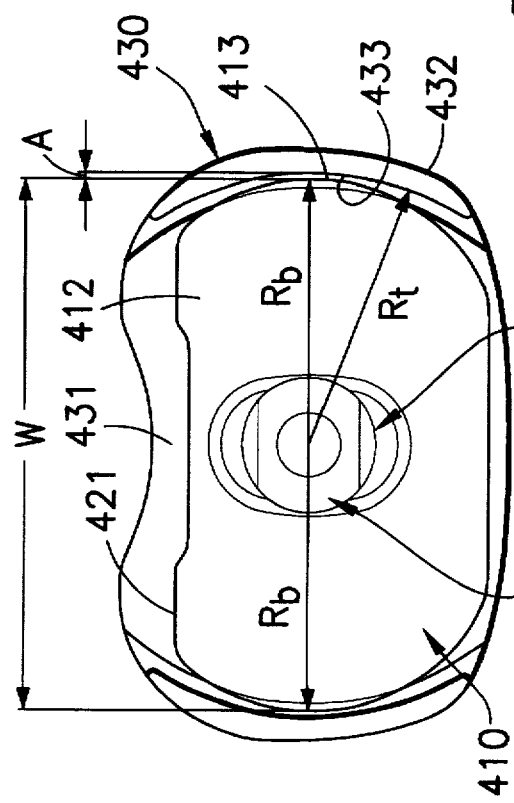
FIG. 14 is a superior view of the tibial platform with a transparent view of the inferior bearing region and the cavity thereof.

FIGS. 14–17 shows superior views of the tibial platform 430 and a transparent view of the inferior bearing region 421 with cavity 416. FIG. 14 shows cavity 416 centered on button 436. In this position the button 436 will fit into the central hole 417 and allow the inferior bearing surface 412 to seat centrally on the load bearing plate 431 of tibial component 430. In this position there will be a clearance with a minimum value of "A" between the thrust surfaces 413 of the bearing and the faces 433 of the side walls 432 of the tibial platform 430.

Figure 15:
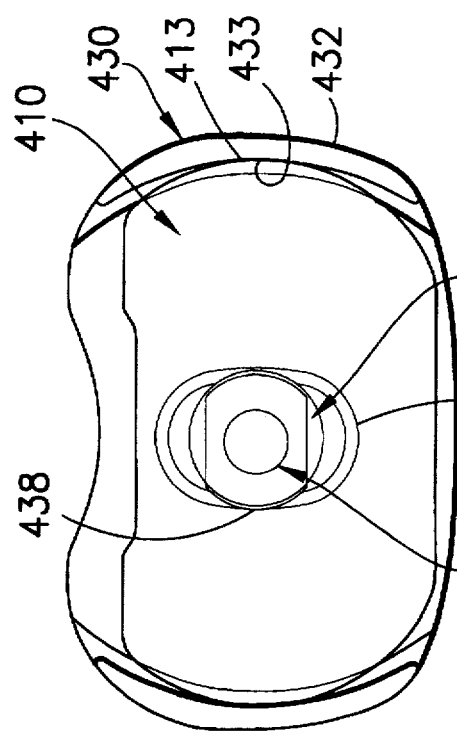
FIG. 15 is a superior view similar to FIG. 14 but with the bearing moved in a medial-lateral direction relative to the tibial platform.

Under the action of M-L shearing forces in the knee the bearing 410 will move medially or laterally relative to the tibial platform 430 until a thrust surface 413 of the bearing 410 with a radius equal to $R_b$ contacts a corresponding face 433 of the tibial platform 430 with a radius $R_r$, as shown in FIG. 15. The oval side walls 418 provide clearance between them and the button side walls 438 in this position so that such medial or lateral motion is permitted.

The values of these radii $R_b$ and $R_r$ are critical to effective functioning of the prosthetic component 100. The embodiment shown uses values of $R_b=0.850"$ and $R_r=1.252"$ or in non-dimensional form a Radius Ratio $R_b/R_r=0.68$. Using a clearance $A=0.025"$ these radii produce a total A-P travel of $C=0.29"$. As noted above, the concave faces 433 of the side walls 432 form segments of the same right circular cylinder radius $R_r$. This cylinder has a diameter of twice $R_r$ which in the example above equals 2.504". The thrust surfaces 413 of the bearing 410 are segments of two right circular cylinders of radius $R_b$. Using the ratios and dimensions set forth above, twice $R_b$ equals only 1.70". The difference between the diameter of the concave faces 433 of the side walls 432 (twice $R_r$) and the sum of the radii of the thrust surfaces 413 (twice $R_b$) is significantly less than twice the clearance A in the example above. This relationship occurs because, as shown most clearly in FIG. 14, the thrust surfaces 413 are generated about centers that are spaced from the medial-to-lateral midpoint of the bearing 410. Thus, again as shown most clearly in FIG. 14, the bearing 410 defines a width W that is greater than twice $R_b$ but less than twice $R_r$ by an amount equal to twice A. These values, excluding the non-dimensional Radius Ratio, are associated with a particular, and most common size tibial component. The values of radii, clearance, and resulting A-P motion can be proportionally scaled to the size of the tibial platform for other sizes. For a particular size, increasing "A" will increase "C" at the expense of increased undesirable M-L play. Decreasing the Radius Ratio will also increase A-P motion but at the expense of an undesirable increase in the contact stress. The values above represent a preferred embodiment although vales of "A" from 0.020" to 0.060" and Radius Ratio from 0.20 to 0.90 are useful.

Figure 17:
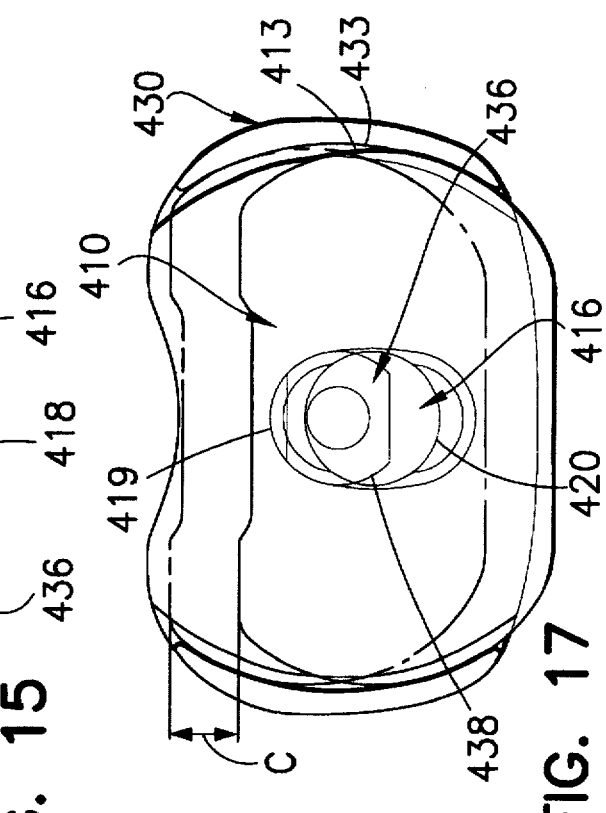
FIG. 17 is a superior view similar to FIG. 16, but showing the bearing at the maximum anterior position relative to the tibial platform.
Figure 16:
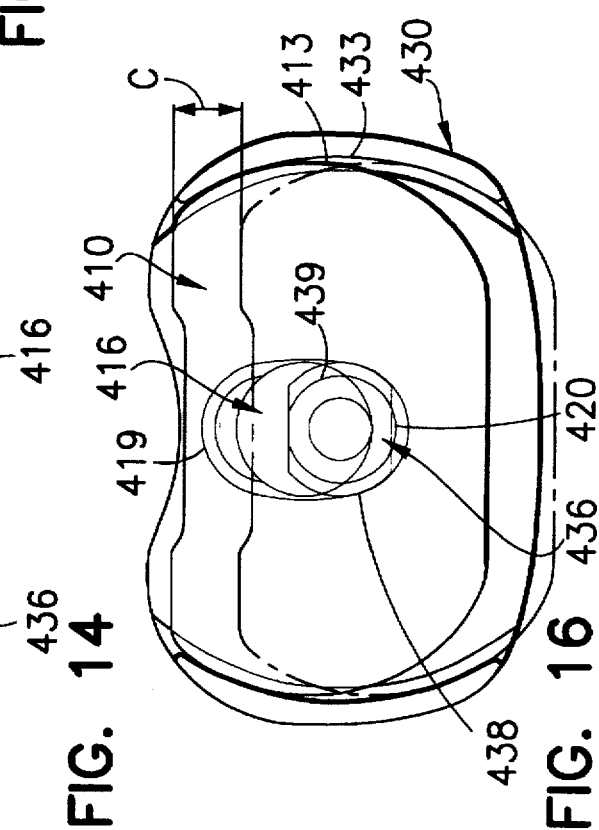
FIG. 16 is a superior view similar to FIG. 14 but showing the bearing at the most posterior position relative to the tibial platform.

FIGS. 16 and 17 show the most posterior and anterior positions of the bearing 410 relative to the tibial platform 430 respectively. In these positions contact between the thrust surfaces 413 and side wall 433 can restrict further A-P motion. Alternately contact between the button side walls 438 and the cylindrical ends 419 of the cavity 416 can stop the motion. In these positions the ridges 420 of cavity 416 engage the recess groove 439 in the button 436. This engagement prevents dislocation of the bearing 410 from the tibial platform in these positions by resisting lifting forces resulting from tilting of the bearing 410 on the load bearing plate 431 of the tibial platform 430. It is these positions that produce the tilting forces associated with motion limitation which may produce such dislocation. At the extremes of A-P motion no side clearance is needed between the button side walls 438 and the cylindrical ends 419 since in these positions there is no M-L side play between the thrust surfaces 413 and the side walls 433.

The use of a separate means for resisting medial-lateral thrust loads and retention against bearing lifting has the advantage that the thrust surfaces can be simple right circular cylinders which can be accurately made at reasonable cost thereby providing greater conformity of the thrust surfaces reducing contact stress and wear. The lift retention surfaces need not be accurate since they only act at the extremes of motion and are not subject to significant sliding or load.

The bearing 410 is free to rotate relative to the tibial platform 430 on the load bearing plate 431 about an axis normal to that plate for all positions of the bearing shown, and any other position of the bearing.

The preferred embodiment described above is intended for cases where there is a viable posterior cruciate ligament but no viable anterior cruciate ligament. Such cases account for about 65% of knee replacement surgeries. The device, because it limits A-P motion, and thus provides some A-P stability, is also useful for most cases where neither the posterior nor anterior cruciate ligament are viable. Such cases account for about 30% of knee replacement surgery. Where the posterior cruciate ligament is absent or not viable, some surgeons may prefer to use a device which does not allow significant A-P motion, and thus provides enhanced A-P stability.

Figure 18:
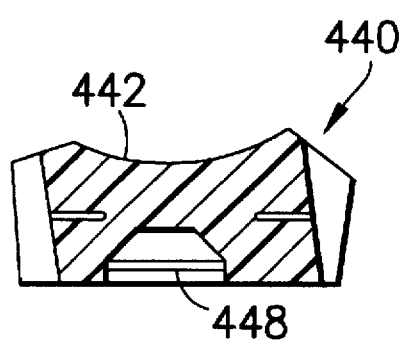
FIG. 18 is a saggital cross-sectional view of an alternate bearing.
Figure 19:
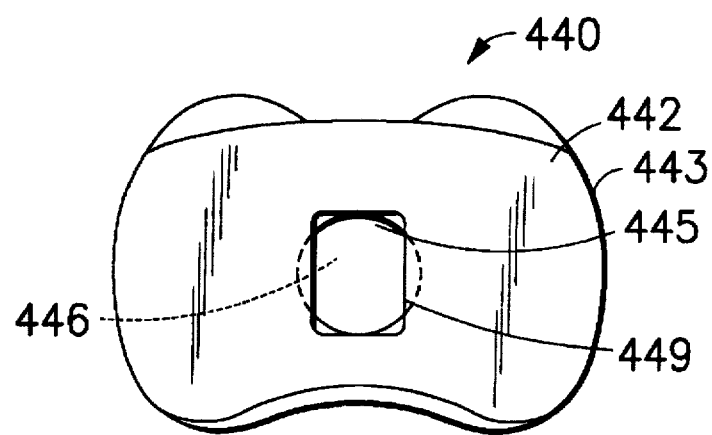
FIG. 19 is an inferior view of the bearing shown in FIG. 18.
Figure 20:
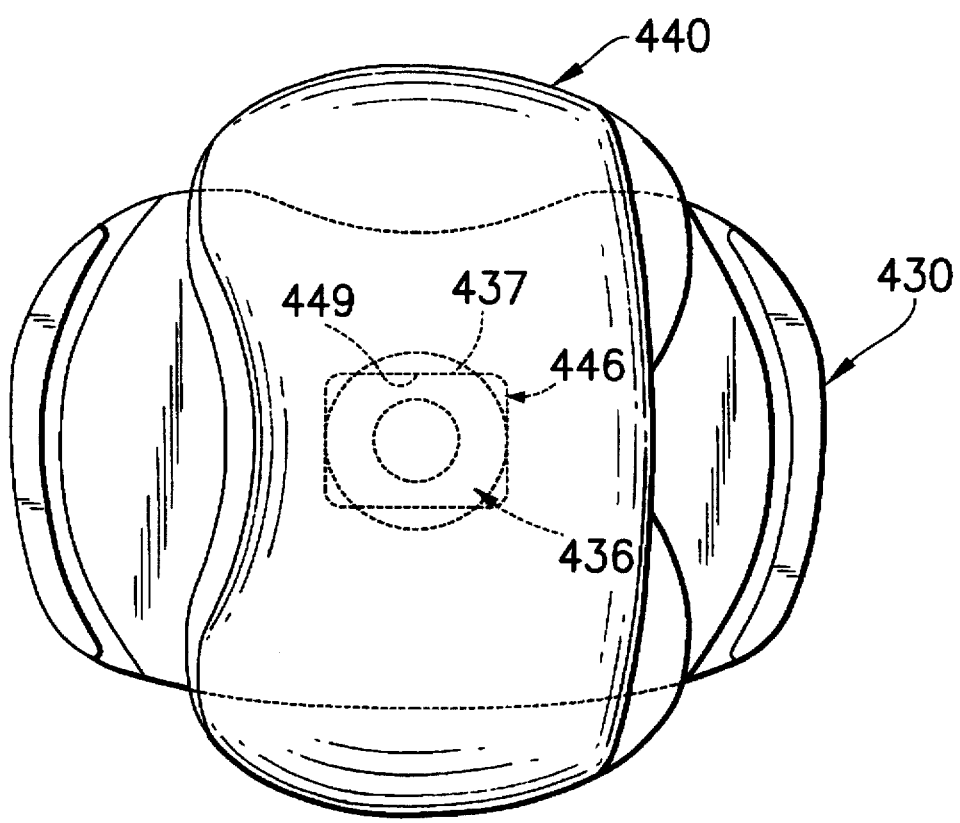
FIG. 20 is a superior view of the tibial platform and a transparent view of the inferior bearing region at an intermediate step during their assembly.

An alternate, Rotational Bearing, embodiment which allows only axial rotation of a rotational bearing is shown in FIGS. 18 and 19 and which are a coronal cross-section and inferior view respectively of a rotational bearing 440. This rotational bearing 440 contains a rotational inferior bearing surface 442 and rotational thrust surfaces 443 which are segments of the same right circular cylinder of a radius about 0.005" smaller than $R_t$. The rotational bearing 440 may also contain a rotational cavity 445 with a rectangular hole 446 and a rotational circular hole 446 with rotational ridges 448. FIGS. 20 and 21 show the method of installation of rotational bearing 440 onto the tibial platform 430. The rotational bearing 440 is positioned as shown in FIG. 20 so the long sides 449 of the rectangular hole 446 are aligned with the flats 437 on button 438. The button will now enter the rotational circular hole 446 and allow the rotational inferior bearing surface 442 to engage the tibial load bearing plate 431. The rotational bearing 440 is then rotated 90° to the position shown in FIG. 21. This rotation causes the rotational ridges 448 to engage the recess groove 439 in button 436. This retains the rotational bearing 440 against dislocation from the tibial platform 430 in normal use since 90° of bearing rotation is not encountered in the human knee. In this embodiment $R_b$ is about equal to $R_t$ and thus significant A-P motion is inhibited. Only axial rotation occurs. Shearing loads are easily carried by the congruent contact associated with rotational thrust surfaces 443 and faces 433.

Although mobile bearings are preferred over fixed bearings in knee and other joints resulting in lower articulating contact stresses and wear, due to the fear of dislocation and general suspicion of moving parts by orthopaedic surgeons, mobile bearings are limited to only about 5% of the market in the U.S., and less than 10% in Europe. Thus a third, Fixed Bearing, embodiment is useful where the tibial platform 430 is used with a non-mobile, or fixed, bearing. FIGS. 22 and 23 show a saggital and inferior view of a fixed bearing 450. The assembled bearing and platform are shown in FIG. 24. The fixed bearing 450 consists of a fixed tibial articulating surface 451, not conforming to the femoral articulating art surface 201 a fixed inferior bearing surface 452, fixed thrust surfaces 453 of radius $R_t$ with end recesses 454 and other features similar to the other bearing embodiments. The fixed bearing 450 may also include a cavity 456 with an internal ridge 460.

The fixed bearing 450 is assembled to the tibial platform by aligning the end recesses 454 of the bearing with side wall ends 434 of the tibial platform 430, and engaging, when present, the button 436 of the platform with the cavity 456 in the fixed inferior bearing surface 452. The bearing is then pressed into the platform spreading the internal ridge 460 in the plastic bearing unit it spreads over the button side walls 438 and the ridge engages the recess groove 439 in the button retaining the bearing in the platform.

Both mobile and fixed bearing types can all be used as elements of a knee system consisting of different types of femoral components with different fixation options but with similar articulating surfaces and a series of tibial components. A system employing both bearing types provides greater options for an orthopaedic surgeon or salesman than the typical system which is limited to only fixed or mobile bearing type.

A feature of the tibial platform 430 is that it can accept all three embodiments of the bearing. Normally each bearing type has a different tibial platform. This universality has two benefits. First such a universal platform in a system of tibial implants minimizes inventory requirements reducing the cost of the use of the system while providing maximum options for surgeon preference of bearing type. Secondly in the event of difficulty with one bearing type, a different bearing type can be substituted without removal and exchange of the tibial platform. This might occur, for example, in case of a posterior cruciate rupture producing unacceptable A-P instability. The surgeon could then replace the A-P Glide bearing with a Rotational bearing. Another example is a case of rare rotational instability associated with a mobile bearing. In such a situation the mobile bearing can be replaced by a fixed bearing again without removal and replacement of the tibial platform.

An alternate embodiment of the button retention means useful primarily for the Rotating and Fixed bearings is shown in FIGS. 25–27. As shown in FIG. 26 an alternate tibial platform 460 has a load bearing plate 461 and a retaining button 466 with retaining side walls 468 and a recess groove 469 with a retaining face 467. The alternate bearing 470, shown in FIG. 25, has an inferior bearing surface 472 and a retaining cavity 476 with a segmented flexible retaining lip 477 with a retaining end 478.

To assemble the alternate bearing and tibial platform the retaining cavity is placed onto the retaining button. As the alternate bearing moves downward toward the alternate tibial platform the retaining end 478 of the flexible segmented lip 477 engages the retaining side walls 468 and are flexed outward allowing the motion to continue. When the inferior bearing surface 472 is seated on the tibial load bearing surface 461 the retaining end will be clear of the retaining side wall and will be free to move inwardly. After this inward motion the retaining end 478 engages the retaining face 467. The lip and face are configured such that upward motion of the bearing relative to the tibial platform is prevented in that such motion would tend to produce inward motion of the lip, which motion is prevented by the contact between the lip end and retaining face.

The preferred material for the metallic components is titanium alloy coated with a titanium nitride ceramic. Cobalt chromium alloy is however used much more extensively, and is a suitable material. The preferred plastic is wear resistant, and surgical, grade polyethylene. Other materials may also be useful.

Although the embodiments shown are for knee replacement such designs are also useful for other condylar joints such as the finger, thumb, toes, elbow and ankle.

I claim:

1. A prosthetic joint replacement for a condylar joint comprising:
    a first prosthetic component having a bone attachment portion for attachment to a first bone of said condylar joint and having an articular surface;
    a second prosthetic component having a bone attachment portion for attachment to a second bone of said condylar joint, said second prosthetic component further having a bearing surface and medial and lateral side walls projecting from said bearing surface, each said side wall having a concave surface, said concave surfaces defining arc segments of a single right circular cylinder having a selected radius and being generated about a selected center on said second prosthetic component; and
    a bearing disposed between the first and second prosthetic components, said bearing having a first bearing surface in articular bearing relationship with the articular surface of said first prosthetic component, a second bearing surface slidably and rotatably engaged with the bearing surface of said second prosthetic component, and medial and lateral thrust surfaces facing the respective medial and lateral side walls of the second prosthetic component, the thrust surfaces defining arc segments of two right circular cylinders which have selected radii less than the radius of said concave surfaces of said second prosthetic component and which are generated about separate medial and lateral centers disposed respectively between the center of the second prosthetic component and the medial and lateral side walls thereof to permit a selected small medial-lateral sliding movement of said bearing between said side walls of said second prosthetic component and a selected substantially larger anterior-posterior sliding movement of said bearing on said second prosthetic component.

2. The prosthetic joint replacement of claim 1, wherein the concave surfaces of said side walls of said second prosthetic component define a radius $R_r$, and wherein the thrust surfaces of the bearing define radii $R_b$, the radii $R_r$ and $R_b$ being selected to define a radius ratio $R_b/R_r$ in the range of 0.2–0.9.

3. The prosthetic joint replacement of claim 2, wherein the radius ratio $R_b/R_r$ is approximately equal to 0.68.

4. The prosthetic joint replacement of claim 1, wherein the bearing is dimensioned relative to the side wall surfaces of said second prosthetic component to permit medial and lateral clearances between said thrust surfaces and said respective side wall surfaces of between 0.020" and 0.060".

5. The prosthetic joint replacement of claim 4, wherein the medial and lateral clearances are selected to be approximately 0.025", and wherein the bearing is dimensioned relative to the side wall surfaces of said second prosthetic component to enable a total anterior-posterior sliding movement of approximately 0.29".

6. The prosthetic joint replacement of claim 1, wherein said second prosthetic component includes a bone attachment portion facing away from said bearing surface thereof for securely attaching said second prosthetic component to a bone.

7. The prosthetic joint replacement of claim 1, wherein the bearing is dimensioned relative to the side wall surfaces of said second prosthetic component to enable a total anterior-posterior sliding movement of said bearing on said second prosthetic component approximately 5.8 times greater than a sum of medial-lateral said bearing and said side walls of said second prosthetic component.

8. A prosthetic joint replacement for a condylar joint comprising:
    a first prosthetic component having a bone attachment portion for attachment to a first bone of the condylar joint and having an articular surface;
    a second prosthetic component having a second bone attachment portion for attachment to a second bone of the condylar joint, said second prosthetic component further having an opposed substantially planar bearing surface, side walls projecting from said bearing surface of said second prosthetic component, each said side wall having a concave surface orthogonal to said bearing surface of said second prosthetic component, said concave surfaces defining arc segments of a single right circular cylinder of radius $R_r$; and
    a plastic bearing disposed between said first and second prosthetic components, said bearing having a first bearing surface in articular bearing engagement with the articular surface of the first prosthetic component and a second bearing surface slidably and rotatably disposed on the bearing surface of said second prosthetic component, thrust surfaces aligned orthogonally to said second bearing surface and defining arc segments of two right circular cylinders having radii $R_b$, said radii $R_b$ being less than $R_r$, the thrust surfaces being generated about centers that are spaced in a first direction to define a selected width for said bearing in said first direction that is greater than twice $R_b$, but less than twice $R_r$, for permitting sliding movement of said bearing in directions parallel to said first direction which is significantly less than sliding movement of said bearing permitted in a second direction orthogonal to said first direction.

9. The prosthetic joint replacement of claim 8, wherein $R_r$ exceeds one-half the width of the bearing by a distance in the range of 0.020" to 0.060".

10. The prosthetic joint replacement of claim 9, wherein the distance is approximately 0.025", and wherein the thrust surfaces of said plastic bearing are dimensioned and disposed to permit a total sliding travel of said bearing in said second direction of approximately 0.29".

11. The prosthetic joint replacement of claim 8, wherein the radius $R_r$ of said second prosthetic component and the radii $R_b$ of said bearing are selected to define a radius ratio $R_b/R_r$ in the range of 0.20–0.90.

12. The prosthetic joint replacement of claim 8, wherein the radius ratio $R_b/R_r$ is approximately equal to 0.68.

13. The prosthetic joint replacement of claim 8, wherein said sliding movement in said anterior and posterior directions exceed a sum of the M-L clearances by approximately a factor of 5.8.

14. A prosthetic joint replacement for a condylar joint comprising:

a first prosthetic component having a bone attachment portion for attachment to a first bone of the condylar joint and having an articular surface;

a second prosthetic component having a bone attachment portion for attachment to a second bone of the condylar joint, a pair of side walls projecting away from said bone attachment portion, each said side wall having a concave surface, said concave surfaces of said side walls facing one another, a bearing surface facing away from said bone attachment portion and extending between the respective concave surfaces of said side walls; and a single bearing disposed between said first and second prosthetic components, said bearing having a first bearing surface in articular bearing engagement with the articular surface of the first prosthetic component, a pair of convex thrust surfaces disposed between the side walls of the second prosthetic component and a second bearing surface extending continuously between the convex thrust surfaces, said second bearing surface being slidably and rotatably engaged with the bearing surface of said second prosthetic component and the convex thrust surfaces facing the respective concave surfaces of the side walls of the second prosthetic component, the convex thrust surfaces being dimensioned and configured relative to said facing concave surfaces of said side walls for all positions of said bearing on the second prosthetic component to permit substantially greater sliding movement of said bearing on said second prosthetic component along a first axis than along a second axis orthogonal to said first axis.

15. The prosthetic joint replacement of claim 14, wherein the bearing is dimensioned and configured to define clearances between said thrust surfaces and the opposed side walls of said second prosthetic component in a range of 0.020" and 0.060" as measured in a direction parallel to said second axis.

16. The prosthetic joint replacement of claim 15, wherein the thrust surfaces of said bearing are dimensioned and configured to permit a range of movement of approximately 0.29" as measured in a direction parallel to said first axis.

17. The prosthetic joint replacement of claim 14, wherein the concave surfaces of said side walls of said platform are segments of a single cylinder, and wherein the thrust surfaces of the bearing are arc segments of two separate cylinders, the thrust surfaces defining radii less than the arc segment of the concave surfaces of the side walls.

18. The prosthetic joint replacement of claim 14, further comprising means for preventing dislocation between the second bearing surface of the bearing and the bearing surface of the second prosthetic component, the means for preventing dislocation being spaced from the thrust surfaces of the bearing and spaced from the concave surfaces of the second prosthetic component.

19. The prosthetic joint replacement of claim 14, wherein the thrust surfaces are dimensioned and configured relative to said side walls to permit anterior and posterior sliding movement of said bearing on said second prosthetic component approximately 5.8 times greater than a sum defined by medial and lateral clearances between said bearing and said side walls of second prosthetic component.

20. A prosthetic joint replacement for a condylar joint comprising:

a first prosthetic component having a bone attachment portion for attachment to a first bone of the condylar joint and an articular surface;

a second prosthetic component having a bone attachment portion for attachment to a second bone of the condylar joint and a substantially planar bearing surface;

a plastic bearing disposed between said first and second prosthetic components, said bearing having a first bearing surface in articular bearing engagement with the articular surface of the first prosthetic component and a second bearing surface disposed in sliding and rotary bearing engagement on the bearing surface of said second prosthetic component;

sliding limitation means on said second prosthetic component and said bearing for limiting sliding movement therebetween, said sliding limitation means being disposed respectively at medial and lateral sides on said second prosthetic component and said bearing; and dislocation prevention means spaced from said sliding limitation means and disposed on the respective second prosthetic component and the bearing at locations generally centrally between medial and lateral sides thereof for preventing dislocation of the bearing surface of said second prosthetic component from the second bearing surface of said plastic bearing while permitting rotary movement between said plastic bearing and said second prosthetic component.

21. The prosthetic joint replacement of claim 20, wherein the ridge of the bearing is a segmented ridge defining a plurality of independently resiliently deflectale ridge segments.

22. The prosthetic joint replacement of claim 20, wherein the sliding limitation means comprise medial and lateral side walls projecting from the bearing surface of said second prosthetic component, said medial and lateral side walls each having an anterior end, a posterior end and a concave surface therebetween, said concave surfaces of said medial and lateral side walls facing one another, the sliding limitation means further comprising medial and lateral thrust surfaces defining respective medial and lateral extremes of said bearing and facing the respective medial and lateral side walls of the first prosthetic component.

23. The prosthetic joint replacement of claim 22, wherein the concave surfaces of the medial and lateral side walls of the second prosthetic component define arc segments of a single right circular cylinder aligned orthogonally to the planar bearing surface of said second prosthetic component.

24. The prosthetic joint replacement of claim 23, wherein the thrust surfaces of said bearing define arc segments of two right circular cylinders having radii smaller than the radius of the concave surfaces of said second prosthetic component.

25. The prosthetic joint replacement of claim 22, wherein the dislocation prevention means comprises a button projecting from said planar bearing surface of said second prosthetic component, said button including an undercut defining a reduced cross-sectional region, said dislocation prevention means further including a cavity extending into said second bearing surface of said bearing and having ridge means engageable with the undercut of said button for preventing dislocation of said second bearing surface from said bearing surface of said second prosthetic component.

26. The prosthetic joint replacement of claim 20, wherein the dislocation prevention means comprises a button projecting from the planar bearing surface of the second prosthetic component, said button including an undercut defining a reduced cross-sectional region, said dislocation prevention means further including a cavity extending into said second bearing surface of said bearing, a plurality of resilient independently deflectable ridge segments adjacent said cavity and engageable with the undercut for preventing dislocation.

27. The prosthetic joint replacement of claim 20, wherein said sliding limitation means on said second prosthetic component and said bearing permits sliding movement in anterior and posterior directions approximately 5.8 times greater than a sum of lateral and medial clearances between said bearing and said sliding limitation means.

28. A system of joint replacement prosthetic components for condylar joints comprising:
   a first prosthetic component attachable to a first bone of one said condylar joint, said first prosthetic component having an articular surface;
   a second prosthetic component attachable to a second bone of one said condylar joint, said second prosthetic component further having a bearing surface; and
   a plurality of bearings, each said bearing having a first bearing surface for articular bearing engagement with the articular surface of said first prosthetic component, each said bearing further having a second bearing surface, the second bearing surface of at least one said bearing in said system being fixedly engageable with the bearing surface of said second prosthetic component for defining a fixed bearing joint replacement, the second bearing surface of at least a second bearing in said system being rotatably engageable with the bearing surface of said second prosthetic component for defining a rotating bearing joint replacement, and the second bearing surface of at least a third bearing in said system being slidably engageable with the bearing surface of said second prosthetic component for defining a sliding bearing joint replacement.

29. A prosthetic joint replacement for a condylar joint comprising:
   a first prosthetic component having a bone attachment portion for attachment to a first bone of said condylar joint and having an articular surface;
   a second prosthetic component having a bone attachment portion for attachment to a second bone of said condylar joint, said second prosthetic component further having a bearing surface and medial and lateral side walls projecting from said bearing surface, each said side wall having an anterior end, a posterior end and a concave surface therebetween, said concave surfaces defining arc segments of a single right circular cylinder, a button projecting from said bearing surface at a location concentric with said concave surfaces; and
   a bearing disposed between the first and second prosthetic components, said bearing having a first bearing surface in articular bearing relationship with the articular surface of said first prosthetic component, a second bearing surface slidably and rotatably engaged with the bearing surface of said second prosthetic component, and medial and lateral thrust surfaces facing the respective medial and lateral side walls of the second prosthetic component, the thrust surfaces defining arc segments of two right circular cylinders which are dimensioned and disposed to permit a selected small medial-lateral sliding movement of said bearing between said side walls of said second prosthetic component and a selected substantially larger anterior-posterior sliding movement of said bearing on said second prosthetic component, a cavity extending into said second bearing surface at a location generally centrally between said thrust surfaces, said button of said second prosthetic component being slidably and rotatably engaged within said cavity.

30. The prosthetic joint replacement of claim 29, wherein said cavity and said button are dimensioned to provide medial and lateral clearances no less than the medial and lateral clearances between the thrust surfaces of the bearing and the side walls of the second prosthetic component.

31. The prosthetic joint replacement of claim 29, wherein the cavity is of generally oval shape with a long axis aligned in an anterior-posterior direction.

32. The prosthetic joint replacement of claim 29, wherein said button includes a groove extending parallel to said bearing surface of said second prosthetic component, said bearing including a ridge defining a reduced cross-sectional entry to said cavity, said ridge being selectively engageable with said groove for resisting dislocation of the bearing surface of the bearing from the bearing surface of the second prosthetic component.

33. The prosthetic joint replacement of claim 32, wherein said button includes a pair of flats aligned in a medial-lateral direction and spaced apart a distance less than the reduced cross-sectional entry to the cavity of said bearing.

34. A prosthetic joint replacement for a condylar joint comprising:
   a first prosthetic component having a bone attachment portion for attachment to a first bone of the condylar joint and having an articular surface;
   a second prosthetic component having a second bone attachment portion for attachment to a second bone of the condylar joint, said second prosthetic component further having an opposed substantially planar bearing surface, medial and lateral side walls projecting from said bearing surface of said second prosthetic component, each said side wall having an anterior end, a posterior end and a concave surface orthogonal to said bearing surface of said second prosthetic component, said concave surfaces defining arc segments of a single right circular cylinder of radius $R_r$, a button projecting from said bearing surface at a location concentric with said concave surfaces; and
   a plastic bearing disposed between said first and second prosthetic components, said bearing having a first bearing surface in articular bearing engagement with the articular surface of the first prosthetic component and a second bearing surface slidably and rotatably disposed on the bearing surface of said platform, medial and lateral thrust surfaces aligned orthogonally to said second bearing surface and defining arc segments of two right circular cylinders having radii $R_b$, said radii $R_b$ being less than $R_r$, the thrust surfaces being spaced in a medial-to-lateral direction to define selected M-L clearances between said bearing and the respective medial and lateral side walls of said platform, said radii $R_b$ being selected relative to said radius $R_r$ and relative to said M-L clearances to permit sliding movement in anterior and posterior directions which significantly exceed the M-L clearances, a cavity extending into said second bearing surface at a location generally centrally between said thrust surfaces, said button of said second prosthetic component being slidably and rotatably engaged within said cavity.

35. The prosthetic joint replacement of claim 34, wherein the cavity and the button are lockingly engaged with one another for maintaining the second bearing surfaces of said plastic bearing and said second prosthetic component in sliding engagement with one another.

36. The prosthetic joint replacement of claim 34, wherein the cavity is elongate for permitting substantially greater sliding movement in anterior and posterior directions than in medial and lateral directions.

37. A prosthetic joint replacement for a condylar joint comprising:

a first prosthetic component having a bone attachment portion for attachment to a first bone of said condylar joint and having an articular surface;

a second prosthetic component having a bone attachment portion for attachment to a second bone of said condylar joint, said second prosthetic component further having a bearing surface and first and second spaced apart side walls projecting from said bearing surface, said first and second side walls having first and second concave surfaces respectively defining arc segments of a single right circular cylinder; and a bearing disposed between the first and second prosthetic components, said bearing having a first bearing surface in articular bearing relationship with the articular surface of said first prosthetic component, a second bearing surface slidably and rotatably engaged with the bearing surface of said second prosthetic component, and first and second thrust surfaces facing the respective first and second side walls of the second prosthetic component and defining a width for the bearing, the thrust surfaces defining arc segments of two right circular cylinders having radii less than one-half the width of the bearing to permit a selected small sliding movement of said bearing in a direction parallel to said width and between said side walls of said second prosthetic component and a selected substantially larger sliding movement of said bearing on said second prosthetic component in a direction orthogonal to the width.

38. A system of joint replacement prosthetic components for condylar joints comprising:

a first prosthetic component attachable to a first bone of one said condylar joint, said first prosthetic component having an articular surface;

a second prosthetic component attachable to a second bone of one said condylar joint, said second prosthetic component further having a bearing surface; and a plurality of bearings, each said bearing having a first bearing surface for articular bearing engagement with the articular surface of said first prosthetic component, each said bearing further having a second bearing surface engageable with the bearing surface of said second prosthetic component, at least a first bearing in said plurality being configured for providing a first number of degrees of freedom of movement of said first bearing relative to said second prosthetic component and at least a second bearing of said plurality being configured for permitting a second number of degrees of freedom of movement of said second bearing relative to said second prosthetic component.

39. A system as in claim 38, wherein said first bearing is fixedly engaged with said second prosthetic component for providing zero degrees of freedom of movement of said first bearing relative to said platform, and wherein said second bearing is configured for providing at least one degree of freedom of movement of said second bearing relative to said second prosthetic component.

40. The system of claim 39, wherein said second bearing is configured for rotation relative to said second prosthetic component about a fixed axis.

41. The system of claim 39, wherein the second bearing is configured for slidable movement on the bearing surface of said second prosthetic component.

42. The system of claim 38, wherein the first bearing is configured for rotation relative to said second prosthetic component about a fixed axis.

43. The system of claim 42, wherein the second bearing is configured for slidably engaging the bearing surface of said second prosthetic component.

* * * * *